United States Patent [19]

Miyazaki et al.

[11] 4,406,879

[45] Sep. 27, 1983

[54] PHTHALAZINOL PREPARATION

[75] Inventors: Hiroshi Miyazaki, Kawasaki; Taka'aki Ohkuma, Tokyo; Yukiko Minatogawa, Tokorozawa; Hiroshi Ninomiya, Sayama, all of Japan

[73] Assignees: Nippon Kayaku Kabushiki Kaisha; Banyu Pharmaceutical Co., Ltd., both of Tokyo, Japan

[21] Appl. No.: 201,929

[22] Filed: Oct. 29, 1980

[30] Foreign Application Priority Data

Nov. 7, 1979 [JP] Japan ............................... 54-143396

[51] Int. Cl.³ ..................... A61K 9/20; A61K 9/36; A61K 31/495
[52] U.S. Cl. .................................. 424/14; 424/19; 424/35; 424/38; 424/250
[58] Field of Search ..................... 424/14, 19, 35, 38, 424/250, 28

[56] References Cited

U.S. PATENT DOCUMENTS

| | | | |
|---|---|---|---|
| 3,840,662 | 10/1974 | Inoue | 424/250 |
| 3,963,716 | 6/1976 | Inoue et al. | 424/250 |
| 4,059,686 | 11/1977 | Tanaka | 424/19 |
| 4,155,993 | 5/1979 | Belleville | 424/35 |
| 4,226,848 | 10/1980 | Nagai | 424/19 |
| 4,292,299 | 9/1981 | Suzuki | 424/28 X |

FOREIGN PATENT DOCUMENTS

| | | |
|---|---|---|
| 2822882 | 12/1978 | Fed. Rep. of Germany . |
| 2218085 | 9/1974 | France . |
| 1081667 | 8/1967 | United Kingdom . |

Primary Examiner—Anna P. Fagelson
Attorney, Agent, or Firm—Wegner & Bretschneider

[57] ABSTRACT

The present invention relates to a pharmaceutical composition containing (1) 6,8-dimethyl-7-ethoxycarbonyl-4-hydroxymethyl-1-phthalazone, (2) a water-soluble cellulose ether alone or together with a polyhydric alcohol or a pharmaceutical carrier. The pharmaceutical composition is useful for preventing and/or treating cerebral blood vessel disorders, peripheral blood vessel disorders and nerval diseases.

7 Claims, 6 Drawing Figures

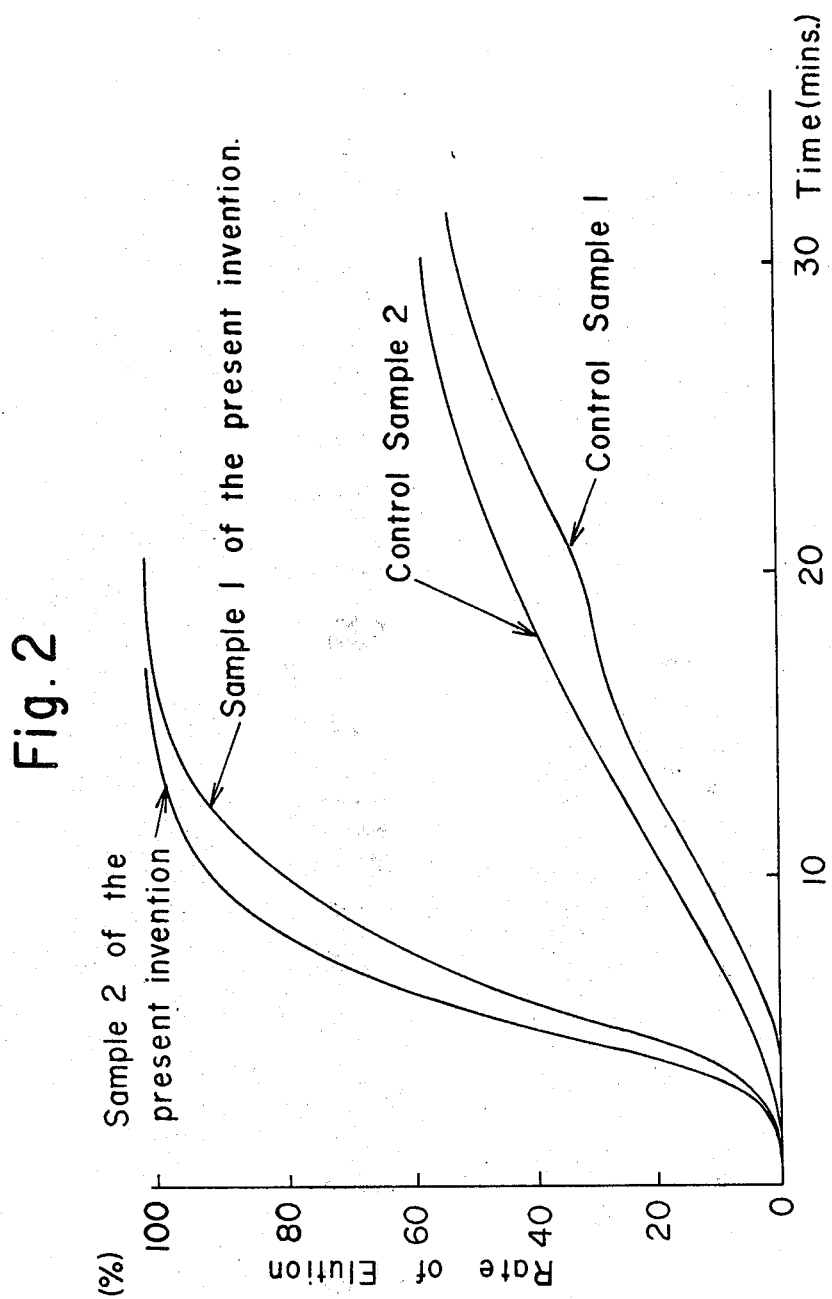

PHTHALAZINOL PREPARATION

BACKGROUND OF THE INVENTION 6,8-Dimethyl-7-ethoxycarbonyl-4-hydroxymethyl-1-phthalazone (hereinafter referred to as "Phthalazinol") is a compound disclosed in the specification of U.S. Pat. No. 3,963,716 (1976) as a medicine for preventing and/or treating cerebral blood vessel disorders such as cerebral hemorrhage, cerebral thrombosis and cerebral arteriosclerosis, peripheral blood vessel disorders such as obstructive arteriosclerosis, and nerval diseases such as spinocerebellar degeneracy, multiple sclerosis, muscular dystrophy and Parkinson's disease.

The inventors have found that though Phthalazinol is absorbed nearly completely (about 100%) when it is administered orally, it is readily metabolized and 4-hydroxymethyl group thereof is converted into inactive 4-carboxyl group by the metabolism with alcohol dehydrogenase in the living body before it arrives at the blood circulation system.

Phthalazinol subjected to the tests at present has a low absorption velocity and, therefore, though Phthalazinol is once absorbed, it is metabolized successively. Consequently, the actual Phthalazinol content of the blood is as small as several tenths of the theoretical value calculated on the assumption that Phthalazinol is not metabolized at all but completely absorbed in the blood.

This phenomenon is generally called "first pass effect".

The inventors hit upon an idea that in order to minimize the first pass effect and to increase the Phthalazinol concentration in the blood, the absorption velocity should be kept at a value far higher than the vanishing velocity thereof in the blood. The inventors further hit upon a good idea that the absorption velocity can be elevated and the Phthalazinol concentration in the blood can be increased by employing characteristic physical properties of Phthalazinol, namely a poor water-solubility (about 0.2 mg/ml. of water at 25° C.) and a low wettability with water.

Generally, as methods of enhancing the absorption velocity of a difficultly water-soluble, difficultly wettable medicine, there may be mentioned the pulverization of the medicine into a fine powder and the addition of a surfactant. According to our experiments on the elution of Phthalazinol treated by the above methods, however, the elution could not be accelerated.

After intensive investigations from the viewpoint of enhancing the contact of Phthalazinol with water, the inventors have found that a composition prepared by adding a water-soluble cellulose ether to Phthalazinol or by adding a polyhydric alcohol to the above two compounds exhibits a remarkably improved elution of Phthalazinol as compared with that obtained by adding a surfactant to Phthalazinol. The present invention has been completed on the basis of this finding.

DETAILED DESCRIPTION OF THE INVENTION

The present invention relates to a novel Phthalazinol preparation.

The preparation of the present invention exhibits a remarkably improved elution of Phthalazinol and its concentration in the blood can remarkably be increased.

The pharmaceutical composition of the present invention comprises (1) 10-90 w/w % of a water-soluble cellulose ether and (2) 90-10 w/w % of Phthalazinol. The composition may further contain a pharmaceutical carrier. In the latter case, the composition comprises (1) 0.1-90 w/w % of a water-soluble cellulose ether, (2) 9.9-89.9 w/w % of a pharmaceutical carrier and (3) 90-10 w/w % of Phthalazinol.

A preferred example of the pharmaceutical composition of the present invention comprises (1) 20-50 w/w % of a water-soluble cellulose ether and (2) 80-50 w/w % of Phthalazinol. A preferred example of the pharmaceutical composition containing the pharmaceutical carrier comprises (1) 0.2-50 w/w of a water-soluble cellulose ether, (2) 80-40 w/w % of Phthalazinol and (3) up to 59.8 w/w % of a pharmaceutical carrier.

The pharmaceutical composition of the present invention exhibits a quite excellent effect particularly when it is used as troches.

If the pharmaceutical composition of the present invention contains a polyhydric alcohol together with the water-soluble cellulose ether, more excellent effects are obtained.

In such a case, the pharmaceutical composition comprises (1) 0.1-85 w/w % of the water-soluble cellulose ether, (2) up to 89.9 w/w % of the polyhydric alcohol and (3) 90-10 w/w % of Phthalazinol. In case the pharmaceutical composition further contains the pharmaceutical carrier, it comprises (1) 0.1-85 w/w % of the water-soluble cellulose ether, (2) 5-89.9 w/w % of the polyhydric alcohol, (3) up to 84.9 w/w % of the pharmaceutical carrier and (4) 90-10 w/w % of Phthalazinol.

In this connection, a preferred embodiment of the pharmaceutical composition comprises (1) 0.2-50 w/w % of a water-soluble cellulose ether, (2) up to 59.8 w/w % of a polyhydric alcohol and (3) 80-40 w/w % of 6,8-dimethyl-7-ethoxycarbonyl-4-hydroxymethyl-1-phthalazone. Another preferred embodiment of the pharmaceutical composition which further contains the pharmaceutical carrier comprises (1) 0.2-35 w/w % of the water-soluble cellulose ether, (2) 5-59.8 w/w % of the polyhydric alcohol, (3) up to 30 w/w % of the pharmaceutical carrier and (4) 80-40 w/w % of Phthalazinol.

Phthalazinol used in the present invention is preferably in the form of a fine powder having a particle size of generally up to 6 μm (average specific surface area diameter), particularly up to 3 μm according to air permeation method.

The Phthalazinol content of the pharmaceutical composition is 10-90 w/w %, preferably 40-80 w/w %, based on the whole composition.

As the water-soluble cellulose ethers, there may be mentioned hydroxypropylmethyl cellulose, hydroxypropyl cellulose and methyl cellulose, etc.

The water-soluble cellulose ether content in the pharmaceutical composition is preferably 0.1-90 w/w %, particularly 0.2-50 w/w %, based on the whole composition.

The alkoxyl contents (%) of the respective water-soluble celluloses (percentages of the molecular weights of the alkoxyl groups based on the molecular weights of the single molecule of alkoxyl-substituted glucose residue contained in the celluloses) [for example, in case of methoxyl group (—OCH$_3$), it is represented by the methoxyl content and in case of hydroxypropoxyl group (—OC$_3$H$_6$OH), it is represented by the hydroxypropoxyl content] and the polymerization degrees are preferably in the ranges as will be described below: In case of the hydroxypropylmethyl cellulose, preferably the methoxyl group content is 26-33%, hydroxypropoxyl group content is 4-14% and polymerization degree is 100-1000. In case of the hydroxypropyl cellulose, preferably the hydroxypropoxyl group content is 4-14% and polymerization degree is 100-1000. In case of the methyl cellulose, preferably the methoxyl group content is 26-33% and polymerization degree is 160-1000.

As the polyhydric alcohols, there may be mentioned, for example, from dihydric alcohols to tetrahydric alcohols. Among them, those which are in liquid form at body temperature (37° C.) are preferred. More particularly, preferred dihydric alcohols include propylene glycol, butylene glycol, polyethylene glycol and polypropylene glycol. Preferred trihydric alcohols include glycerol and preferred tetrahydric alcohols include diglycerol.

Among them, propylene glycol and polyethylene glycol are more preferred.

As the polyethylene glycols, there may be mentioned those having average molecular weights of 200-20,000, preferably 200-6,000, particularly 200-1,000.

The polyhydric alcohol content may be up to 89.9 w/w % based on the whole pharmaceutical composition of the present invention. When the phthalazinol content is 40-80 w/w %, the polyhydric alcohol content is preferably 59.8-5 w/w %, particularly 59.5-5 w/w %.

The water-soluble cellulose ether content of the pharmaceutical composition is at least 0.1 w/w % based on the whole composition. When the phthalazinol content is 40-80 w/w %, the water-soluble cellulose ether content is preferably 0.1-50 w/w %, particularly 0.2-35 w/w %.

An embodiment of the preferred pharmaceutical compositions, particularly the composition for troches, comprises following components (1)-(4):

(1) 0.5-10 w/w % of at least one water-soluble cellulose ether selected from the group consisting of hydroxypropylmethyl cellulose, hydroxypropyl cellulose and methyl cellulose, (2) 5-59.5 w/w % of at least one polyhydric alcohol selected from the group consisting of propylene glycol and polyethylene glycol having an average molecular weight of 200-1000, (3) up to 30 w/w % of the pharmaceutical carrier, and (4) 80-40 w/w % of Phthalazinol.

As the pharmaceutical carrier in the pharmaceutical composition of the present invention, there may be mentioned vehicles, binders, disintegrators, lubricants and adsorbents, etc. generally used for the pharmaceutical preparations.

As the vehicles, there may be mentioned fine crystalline cellulose, mannitol, crystalline lactose, spray-dried lactose, sorbitol, anhydrous calcium phosphate, amylose, pulverized lactose and pulverized sucrose, etc.

As the binders, there may be mentioned water-soluble high molecular substances such as natural gum, cellulose ethers, sodium polyacrylate, polyvinyl pyrrolidone, etc. As the disintegrators, there may be mentioned carboxymethyl cellulose and calcium salt thereof, etc. As the lubricants, there may be mentioned magnesium stearate, etc. As the adsorbents, there may be mentioned silicic acid anhydride, light aluminum silicate, aluminum hydroxide gel, etc.

The preparation of the present invention can be produced by adding Phthalazinol and the water-soluble cellulose ether to water to obtain a slurry, pulverizing the slurry by spray-drying or freeze-drying method, adding a pharmaceutical carrier other than the polyhydric alcohol if necessary and shaping the same into a solid preparation such as tablets, powder or capsules or, alternatively, by dissolving a cellulose ether in a polyhydric alcohol, adding Phthalazinol thereto to obtain a semi-solid mixture and shaping the same into capsules or pulverizing the same with an adsorbents to obtain a powder or, if necessary, shaping the powder further into capsules.

For further reducing the first pass effect, the Phthalazinol preparation of the present invention is used as troches, whereby the elution of Phthalazinol is enhanced, concentration thereof in the blood is remarkably increased and excellent effects are obtained. In such a case, it is preferred to incorporate a water-soluble high molecular substance in the preparation so as to elongate the residence time thereof on the sublingual membranes.

The following experiments will further illustrate that the preparations of the present invention have excellent results.

Parts are given by weight (w/w).

Experiment 1 Elution tests (1) Preparation of samples

Sample 1 of the present invention 50 parts of powdery Phthalazinol [average particle diameter: $2.2\mu$ (specific surface area diameter according to air permeation method)] were added to a solution comprising 5 parts of powdery hydroxypropyl cellulose (trade name: Nisso HPC-SL; a product of Nihon Soda Co., Ltd.) and 92 parts of distilled water. The whole was thoroughly stirred to obtain a homogeneous slurry and then it was spray-dried with a spray-dryer. 55 parts of thus obtained dry powder were added with 25 parts of mannitol and 20 parts of crystalline cellulose (Avicel 101 ®; a product of Asahi Kasei Kogyo Co., Ltd.) and the whole was thoroughly mixed. 120 Milligrams of the resulting mixture were charged in a gelatin capsule to obtain a sample.

Sample 2 of the present invention:

1 Part of powdery hydroxypropyl cellulose was added to 49 parts of Polyethylene glycol 400 to obtain a homogeneous solution. 50 Parts of the same powdery Phthalazinol as that used for the preparation of above Sample 1 were added thereto and the whole was kneaded to obtain a homogeneous mixture. 120 Milligrams of the resulting composition were charged in a gelatin capsule to obtain a sample.

Control sample 1 (containing a surfactant):

A solution comprising 1 part of sucrose/fatty acid esters and 10 parts of water was added to 50 parts of the same powdery Phthalazinol as that used for the preparation of above Sample 1 and the whole was kneaded, dried, sieved through a 30 mesh sieve and added with 48 parts of corn starch and 1 part of magnesium stearate. 120 Milligrams of the resulting mixture were charged in a gelatin capsule to obtain a sample.

Control sample 2 (containing polyethylene glycol alone):

50 Parts of the same powdery Phthalazinol as that used for the preparation of above Sample 1 were added to 50 parts of Polyethylene glycol 400 and the whole was kneaded homogeneously. 120 Milligrams of the resulting composition were charged in a gelatin capsule to obtain a sample.

(2) Method of experiment

900 Milliliters of distilled water were charged in a device as shown in FIG. 1. Basket C containing a sample was rotated at 100 rpm. in a constant temperature bath at 37°±0.5° C. and amounts of the medicine eluted were determined at given time intervals. (see United States Pharmacopeia XIX, p. 651).

(3) Experimental results

The results are shown in FIG. 2. It is apparent from FIG. 2 that amounts of Samples 1 and 2 of the invention eluted 5 minutes after the initiation of the test were 26% and 40%, respectively, while those of Control samples 1 and 2 were as small as 1% and 6%, respectively. 18 Minutes after the initiation, amounts of Samples 1 and 2 of the present invention eluted were nearly 100%, while those of Control samples 1 and 2 were only 28% and 36%, respectively.

Experiment 2 Measurement of concentrations in the human blood (1) Preparation of samples The Phthalazinol composition prepared in Experiment 1 was charged in a gelatin capsule (200 mg) to obtain a troche sample. (The Phthalazinol herein used will be referred to as "$d_0$").

Another sample for the oral administration was prepared in the same manner as in the preparation of Control sample 1 except that Phthalazinol labelled with deuterium ($d_7$) was used.

(2) Method of experiment

Each of samples 1 and 2 of the present invention and Comparative samples 1 and 2 combined with the sample containing $d_7$ was orally administered to healthy male adults. The troche was placed under the tongue and kept from being swallowed for at least 30 minutes. The blood was taken 0.5, 1, 2, 3, 4 and 6 hours after the administration and concentrations of $d_0$ and $d_7$ in the blood were measured at the same time by mass fragment graphy to obtain curves of the concentrations in the blood vs. time. Further, the areas under the serum concentration-time curve were calculated by echelon method to obtain ratios of $d_0$ area to $d_7$ area, namely the ratio of the area under the serum concentration-time curve.

Reasons why the above method is employed will be described below: According to a crossover method generally employed in such experiments, samples are administered to each of the subjects at long time intervals to obtain significant differences in the average values by using numerous subjects. However, according to the crossover method, the true, biological equality between the two samples to be compared can not be realized unfavorably because the physiological conditions of the respective subjects such as amounts of foods taken and conditions of the digestive canals, etc. very every moment. Our method as described above is free of this defect.

(3) Experimental results

The results of the measurement of the concentrations in the human bloods are shown in FIGS. 3-6 and the ratio of the area under the serum concentration-time curve as shown in Table 1.

TABLE 1

| Sample | ratio of the area under the serum concentration-time curve |
| --- | --- |
| Sample 1 of the | 8.21 |

TABLE 1-continued

| Sample | ratio of the area under the serum concentration-time curve |
| --- | --- |
| present invention Sample 2 of the present invention | 13.31 |
| Control sample 1 | 1.98 |
| Control sample 2 | 2.02 |

FIG. 3 shows that the maximum concentration of Sample 1 of the present invention in the blood amounts to 1.0 µg/ml. FIG. 4 shows that the maximum concentration of Sample 2 of the present invention in the blood amounts to 2.45 µg/ml. On the other hand, FIGS. 5 and 6 show that the maximum concentrations of control samples 1 and 2 in the blood were only 0.2 µg/ml. and 0.23 µg/ml, respectively.

It is apparent from Table 1 that the ratio of the area under the serum concentration-time curve of Sample 1 of the present invention was about 4 times as great as the control samples and that the ratio of the area under the serum concentration-time curve of Sample 2 of the present invention was about 6.5 times as great as the control samples.

Thus, as compared with the control samples, the preparations of the present invention have remarkably improved elution properties into water and also remarkably improved concentrations in the blood (4–6.5 times as much). Particularly, the preparation containing the combination of the water-soluble cellulose ether and the polyhydric alcohol has a quite excellent effect, i.e. the maximum concentration in the blood of more than 10 times as great as that of the controls.

The following production examples concretely illustrate the process for producing the preparations of the present invention.

Production Example 1

1 Part of hydroxypropylmethyl cellulose (Shin'etsu Metolose 60SH 400 ®; a product of Shin'etsu Kagaku Co., Ltd.) was added to 10 parts of powdery Phthalazinol having an average particle diameter of about 2.5 µm. THen, 90 parts of water were added thereto to obtain a homogeneous slurry. The slurry was freeze-dried. 55 Parts of the resulting dry powder were added with 20 parts of mannitol and 25 parts of crystalline cellulose (Avicel 101 ®; a product of Ashai Kasei Kogyo Co., Ltd.) to obtain 100 parts of the mixture, which was stirred homogeneously. 200 Milligrams of the resulting composition were charged in a No. 3 hard gelatin capsule.

Production Example 2

1.5 Parts of methyl cellulose (Shin'etsu Metolose SM 100 ®; a product of Shin'etsu Kagaku Co., Ltd.) were added to 15 parts of powdery Phthalazinol having an average particle diameter of about 2.1 µm. Then, 83.5 parts of water were added thereto and the whole was stirred thoroughly to obtain a homogeneous slurry. The slurry was spray-dried with a spray-drier. 55 Parts of thus obtained dry powder were added with 45 parts of Avicel 101 ® and the whole was stirred to obtain a homogeneous mixture. 200 Milligrams of the resulting composition were charged in a No. 3 hard gelatin capsule.

Production Example 3

5 Parts of hydroxypropyl cellulose (Shin'etsu HPC-L; a product of Shin'etsu Kagaku Co., Ltd.) were dissolved in 45 parts of propylene glycol to obtain a homogeneous solution. Then, 50 parts of powdery Phthalazinol having an average particle diameter of about 2.5 μm were added thereto and the whole was stirred thoroughly to obtain a homogeneous slurry. 200 Milligrams of the slurry composition were charged in a No. 4 hard gelatin capsule.

Production Example 4

1 Part of hydroxypropyl cellulose (Nisso HPC-SL) was dissolved thoroughly in 49 parts of polyethylene glycol 400. Then, 50 parts of powdery Phthalazinol having an average particle diameter of about 2.5 μm were added to the solution and the whole was stirred to obtain a homogeneous slurry. 200 Milligrams of the slurry composition were charged in a No. 4 hard gelatin capsule.

Production Example 5

110 Parts of the dry, powdered slurry obtained in Production Example 1 were added with 40 parts of crystalline lactose, 43 parts of Avicel 101 ® (a product of Ashai Kasei Kogyo Co., Ltd.), 4 parts of powdery sodium polyacrylate (average molecular weight: about 5,700,000) and 1 part of fine powdery silicic acid anhydride and the whole was stirred thoroughly. The powdery mixture was added and thereby mixed with 2 parts of magnesium stearate and the resulting mixture was shaped into tablets each weighing 200 mg with a flat pestle having a diameter of 8.5 mm.

Production Example 6

1 Part of hydroxypropylmethyl cellulose (Shin'etsu Metolose 60 SH 400 ®; a product of Shin'etsu Kagaku Co., Ltd.) was added to 12 parts of powdery Phthalazinol having an average particle diameter of about 2.5 μm. Then, 90 parts of water were added thereto to obtain a homogeneous slurry. The slurry was freeze-dried. 65 Parts of the resulting dry powder were added with 7 parts of Polyethylene glycol 6000, 4 parts of mannitol and 1 part of polyvinylpyrrolidone (Kollidon) 25 ®; a product of (C. Holstein Co., Ltd.) and then with 22 parts of crystalline cellulose (Avicel 101 ®; a product of Ashai Kasei Kogyo Co., Ltd.) and 1 part of magnesium stearate to obtain 100 parts of a mixture, which was stirred to obtain a homogeneous mixture and subjected to the powder tableting treatment to obtain tablets each weighing 200 mg.

Production Example 7

0.2 Part of hydroxypropyl cellulose (Shin'etsu HPC-L; a product of Shin'etsu Kagaku Co., Ltd.) was added to 12.8 parts of powdery Phthalazinol having an average particle diameter of about 2.5 μm. Then, 90 parts of water were added thereto to obtain a homogeneous slurry. The slurry was freeze-dried. 65 Parts of the resulting dry powder were added with 8 parts of Polyethylene glycol 4000, 1 part of mannitol and 1 part of polyvinylpyrrolidone (Kollidon 25 ®; a product of C. Holstein Co., Ltd.) and then with 24 parts of crystalline cellulose (Avicel 101 ®; a product of Ashai Kasei Co., Ltd.) and 1 part of magnesium stearate to obtain 100 parts of a mixture, which was stirred to obtain a homogeneous mixture and subjected to the powder tableting treatment to obtain tablets each weighing 200 mg.

Production Example 8

70 Parts of powdery Phthalazinol having an average particle diameter of about 2.5 μm were added to a solution of 30 parts of methyl cellulose (Shin'etsu SM 100 ®; a product of Shin'etsu Kagaku Co., Ltd.) in 30 parts of a solvent comprising distilled water and ethanol (10:90). The whole was thoroughly mixed and shaped into granules by means of a speed mill. The granules were dried. 200 Milligrams of the resulting granules were charged in a No. 3 hard gelatin capsule.

BRIEF DESCRIPTION OF DRAWINGS

FIG. 2 shows the relationships between elution time and elution rate of samples of the present invention and control samples.

Figure 1:
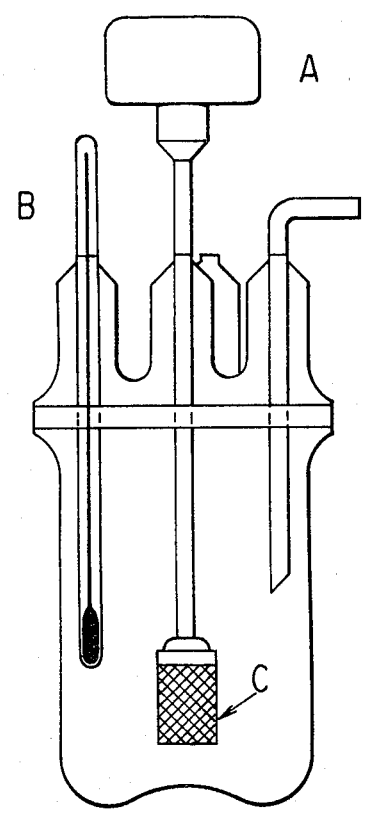
FIG. 1 shows a device for the elution tests, wherein:
  A: Motor,
  B: Thermometer, and
  C: Basket.
Figure 4:
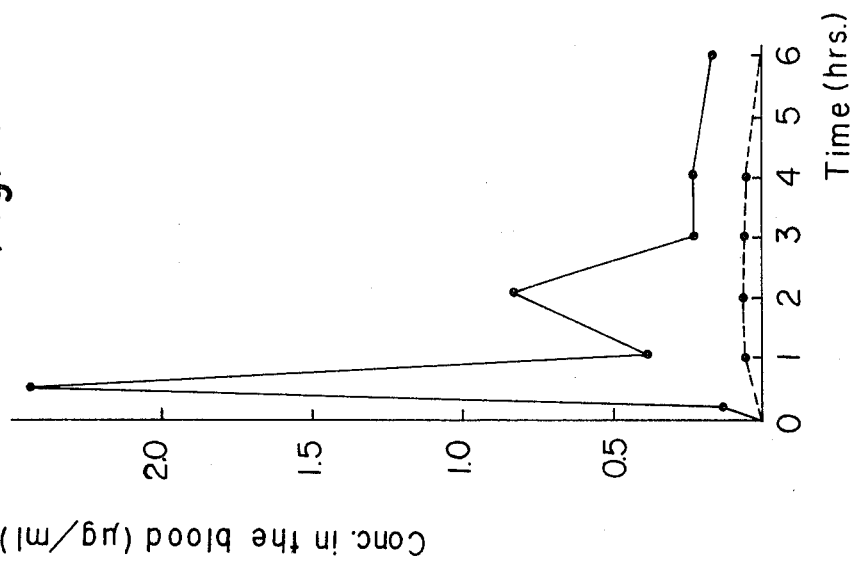
FIGS. 3, 4, 5 and 6 show the relationships between time after the administration and the concentration in the blood of samples 1 and 2 of the present invention and control samples 1 and 2, respectively.
Figure 3:
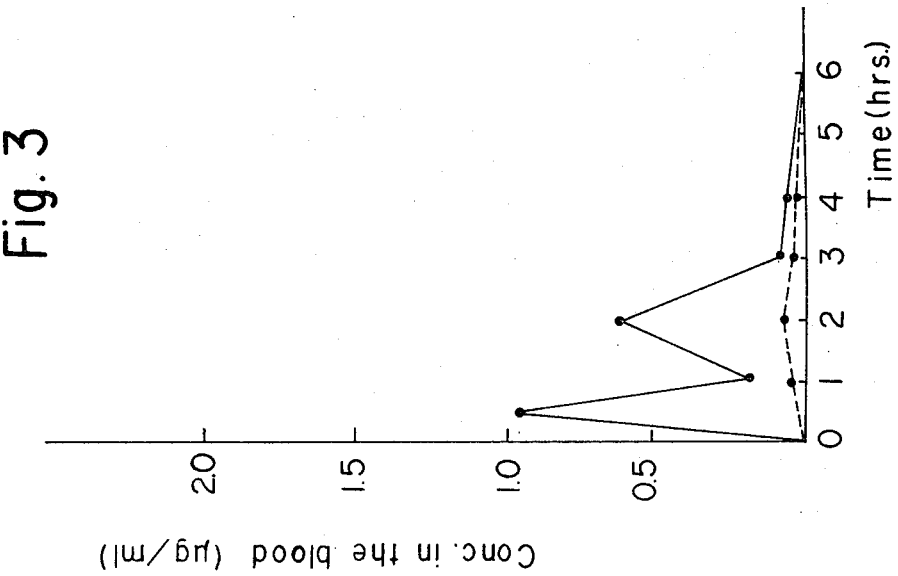
Figure 5:
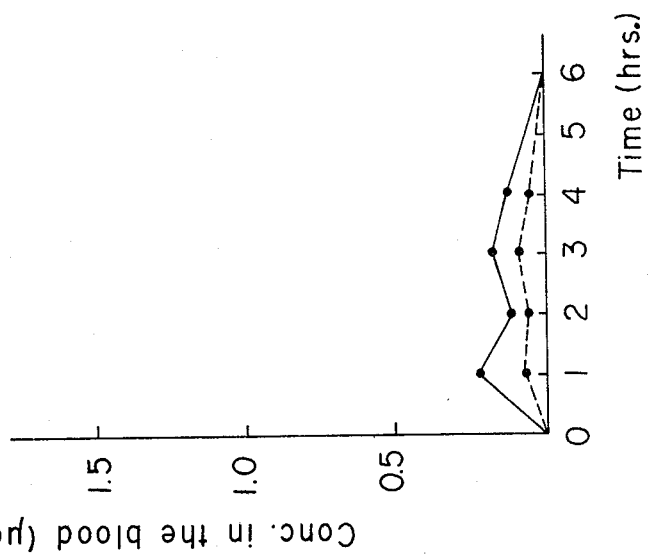
Figure 6:
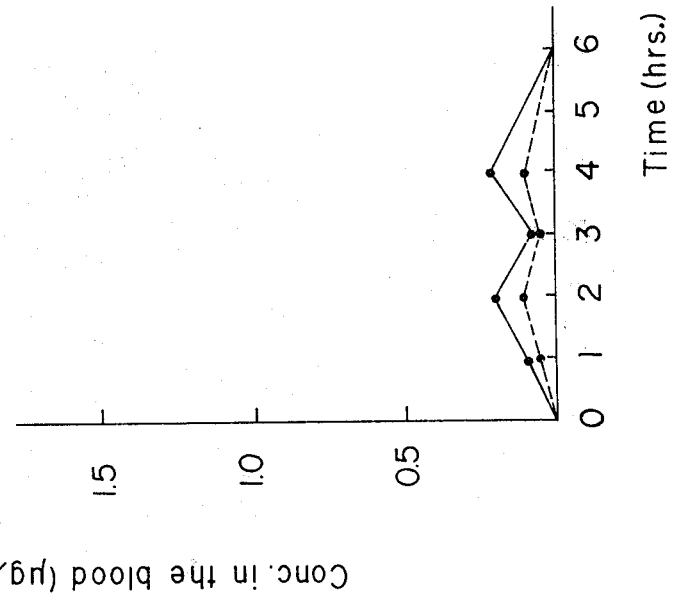

●——$d_0$: An ordinary troche containing Phthalazinol kept below the tongue in the mouth.

▲——$d_7$: Sample for the oral administration prepared in the same manner as in the preparation of control sample 1 except that Phthalazinol labelled with heavy hydrogen was used.

We claim:

1. A pharmaceutical composition comprising: (1) 0.5 to 10 W/W % of a water-soluble cellulose ether, (2) 5 to 59.5 W/W % of a polyhydric alcohol, (3) up to 30 W/W % of a pharmaceutically acceptable carrier and (4) 80 to 40 W/W % of 6,8-dimethyl-7-ethoxycarbonyl-4-hydroxymethyl-1-phthalazone.

2. A pharmaceutical composition according to claim 1, wherein the water-soluble cellulose ether is at least one member selected from the group consisting of hydroxypropylmethyl cellulose, hydroxypropyl cellulose and methyl cellulose.

3. A pharmaceutical composition according to claim 1, wherein the average specific surface area diameter of 6,8-dimethyl-7-ethoxycarbonyl-4-hydroxymethyl-1-phthalazone is up to 3 μm.

4. A pharmaceutical composition according to claim 1, wherein the polyhydric alcohol is dihydric, trihydric or tetrahydric alcohol.

5. A pharmaceutical composition according to claim 1, wherein the polyhydric alcohol is at least one member selected from the group consisting of propylene glycol, butylene glycol, polyethylene glycol having an average molecular weight of 200–6,000, polypropylene glycol, glycerol and diglycerol.

6. A pharmaceutical composition for troches comprising following components (1) through (4):
(1) 0.5–10 w/w % of at least one water-soluble cellulose ether selected from the group consisting of hydroxypropylmethyl cellulose, hydroxypropyl cellulose and methyl cellulose,
(2) 5–59.5 w/w % of at least one polyhydric alcohol selected from the group consisting of propylene glycol and polyethylene glycol having an average molecular weight of 200–1,000,
(3) up to 30 w/w % of a pharmaceutical carrier, and
(4) 80–40 w/w % of 6,8-dimethyl-7-ethoxycarbonyl-4-hydroxymethyl-1-phthalazone.

7. A process for increasing the concentration of 6,8-dimethyl-7-ethoxycarbonyl-4-hydroxymethyl-1-phthalazone in the blood, characterized in that a pharmaceutical composition comprising following components (1) through (4):
(1) 0.5–10 w/w % of at least one water-soluble cellulose ether selected from the group consisting of hydroxypropylmethyl cellulose, hydroxypropyl cellulose and methyl cellulose, (2) 5–59.5 w/w % of at least one polyhydric alcohol selected from the group consisting of propylene glycol and polyethylene glycol of an average molecular weight of 200–1000, (3) up to 30 w/w % of a pharmaceutical carrier, and
(4) 80–40 w/w % of 6,8-dimethyl-7-ethoxycarbonyl-4-hydroxymethyl-1-phthalazone is administered in the form of troches to be kept below the tongue.

* * * * *